(12) United States Patent
Park et al.

(10) Patent No.: US 7,638,312 B2
(45) Date of Patent: Dec. 29, 2009

(54) E.COLI MUTANT CONTAINING MUTANT GENES RELATED WITH TRYPTOPHAN BIOSYNTHESIS AND PRODUCTION METHOD OF TRYPTOPHAN BY USING THE SAME

(75) Inventors: Young-Hoon Park, Seongnam-si (KR); Sang-jo Lim, Yongin-si (KR); Byoung-Hoon Kim, Incheon (KR); Seong-Jun Kim, Suwon-si (KR); Ho-Soo Lim, Icheon-si (KR)

(73) Assignee: CJ Cheiledang Corp. (KR)

( * ) Notice: Subject to any disclaimer, the term of this patent is extended or adjusted under 35 U.S.C. 154(b) by 197 days.

(21) Appl. No.: 10/582,196

(22) PCT Filed: Nov. 23, 2004

(86) PCT No.: PCT/KR2004/003030

§ 371 (c)(1), (2), (4) Date: Jun. 11, 2008

(87) PCT Pub. No.: WO2005/056776

PCT Pub. Date: Jun. 23, 2005

(65) Prior Publication Data

US 2008/0299644 A1    Dec. 4, 2008

(30) Foreign Application Priority Data

Dec. 15, 2003    (KR) ........................ 10-2003-0091398

(51) Int. Cl.
*C12P 13/22*    (2006.01)
*C12N 9/00*    (2006.01)
*C12N 1/20*    (2006.01)
*C07H 21/04*    (2006.01)

(52) U.S. Cl. .................... 435/108; 435/183; 435/252.3; 536/23.2

(58) Field of Classification Search ........................ None
See application file for complete search history.

(56) References Cited

OTHER PUBLICATIONS

Storbakk et al. J Mol Biol. Mar. 15, 1996;256(5):889-96.*

* cited by examiner

*Primary Examiner*—Christian L Fronda
(74) *Attorney, Agent, or Firm*—Buchanan Ingersoll & Rooney P.C.

(57) ABSTRACT

The present invention relates to a Tryptophan-producing *E. coli* mutant strain CJ285 (KCCM-10534) containing single or multi mutant genes related with Tryptophan biosynthesis and production method of Tryptophan using the same. More particularly, DNA base sequences and amino acid sequences aroF, aroG, trpR, and tyrR originated from tryptophan producing *E. coli* mutant strain CJ285 (KCCM-10534) and related with Tryptophan biosynthesis, are disclosed, and *E. coli* CJ285 containing at least one of the mutant genes is cultivated directly in a glucose-containing fermentation medium, whereby L-tryptophan can be accumulated in the culture medium.

2 Claims, 4 Drawing Sheets

Fig. 1 cagaggtaagggttgaaagcgcgactaaattgcctgtgtaaataaaaatgtacgaaatatggat
tgaaaactttactttatggtatcgttacgtcgtcctcgctgaggatcaactatcgcaaacgagc
ataaacaggatcgccatcatgcaaaaagacgcgctgaataacgtacatattaccgacgaacagg
ttttaatgactccggaacaactgaaggccgcttttccattgagcctgcaacaagaagcccagat
tgctgactcgcgtaaaagcatttcagatattatcgccgggcgcgatcctcgtctgctggtagta
tgtggtccttgttccattcatgatccggaaactgctctggaatatgctcgtcgatttaaagccc
ttgccgcagaggtcagcgatagcctctatctggtaatgcgcgtctattttgaaaaacccgtac
cactgtcggctggaaagggttaattaacgatcccatatggatggctcttttgatgtagaagcc
gggctgcagatcgcgcgtaaattgctgcttgagctggtgaatatgggactgccactggcgacgg
aagcgttagatccgaatagcccgcaatacctggcgatctgtttagctggtcagcaattggtgc
tcgtacaacggaatcgcaaactcaccgtgaaatggcctccgggctttccatgccggttggtttt
aaaaacggcaccgacggcagtctggcaacagcaattaacgctatgcgcgccgccgcccagccgc
accgttttgttggcattaaccaggcagggcaggttgcgttgctacaaactcaggggaatccgga
cggccatgtgatcctgcgcggtggtaaagcgccgaactatagccctgcggatgttgcgcaatgt
gaaaagagatggaacaggcgggactgcgcccgtctctgatggtagattgcagccacggtaatt
ccaataaagattatcgccgtcag[tct]gcggtggcagaatccgtggttgctcaaatcaaagat
ggcaatcgctcaattattggtctgatgatcgaaagtaatatccacgagggcaatcagtcttccg
agcaaccgcgcagtgaaatgaaatacggtgtatccgtaaccgatgcctgcattagctgggaaat
gaccgatgccttgctgcgtgaaattcatcaggatctgaacgggcagctgacggctcgcgtggct
taagaggtttattatggttgctgaattgaccgcattacgcgatcaaattgatgaagtcgataaa
gcgctgctgaatttattagcgaagcgtctggaactggttgctgaagtg

Fig. 2 acagtcagaaataatgtggccagttttgtcatttcataggatgctcctgttatggtcgttatg
tcggataacctcttccaacagtgcatttgcaggtgaatataaggcattggtttaagatttcagc
caggttatgaaacgcagcagagaatcttgaaataattaacaaacaaaggagttacagttagaaa
ttgtaggagagatctcgttttcgcgacaatctggcgttttcttgctaattccaggattaatc
[c]gttcatagtgtaaaacccgtttacacattctgacggaagatatagattggaagtattgca
ttcactaagataagtatggcaacactggaacagac<u>atg</u>aattatcagaacgacgatttacgcat
caaagaaatcaaagagttacttcctcctgtcgcattgctggaaaaattccccgctactgaaaat
gccgcgaatacggttgcccatgcccgaaaagcgatccataagatcctgaaaggtaatgatgatc
gcctgttggtt[gcg]attggccca[cgc]tcaattcatgatcctgtcgcggcaaaagagtatg
ccactcgcttgctggcgctgcgtgaagagctgaaagatgagctggaaatcgtaatgcgcgtcta
ttttgaaaagccgcgtaccacggtgggctggaaagggctgattaacgatccgcatatggataat
agcttccagatcaacgacggtctgcgtatagcccgtaaattgctgcttgatattaacgacagcg
gtctgccagcggcaggtgagtttctcgatatgatcaccccacaatatctcgctgacctgatgag
ctggggcgcaattggcgcacgtaccaccgaatcgcaggtgcaccgcgaactggcatcagggctt
tcttgtccggtcggcttcaaaaatggcaccgacggtacgattaaagtggctatcgatgccatta
atgccgccggtgcgccgcactgcttcctgtccgtaacgaaatgggggcattcggcgattgtgaa
taccagcggtaacggcgattgccatatcattctgcgcggcggtaaagagcctaactacagcgcg
aagcacgttgctgaagtgaaagaagggctgaacaaagcaggcctgccagcacaggtgatgatcg
atttcagccatgctaactcgtccaaacaattcaaaaagcagatggatgtttgtgctgacgtttg
ccagcagattgccggtggcgaaaaggccattattggcgtgatggtggaaagccatctggtggaa
ggcaatcagagcctcgagagcggggagccgctggcctacggtaagagcatcaccgatgcctgca
tcggctgggaagataccgatgctctgttacgtcaactggcgaatgcagtaaaagcgcgtcgcgg
g<u>taa</u>ggtttaattgtcggatgcgccgtcagagtggcgtatccgatgaatcaccacaggcctgat
aagtcgcgcagcgtcgcatcaggcaatgtgctccattgttagcaacaaaaaagccgactcactt
gcagtcggctttctcatttaacgaatgacgtttacttcgctttaccctggtttgcaacc

Fig. 3 atggcccaacaatcaccctattcagcagcgatggcagaacagcgtcaccaggagtggttacgtt
ttgtcgacctgcttaagaatgcctaccaaaacgatctccatttaccgttgttaaacctgatgct
gacgccagatgagcgcgaagcgttggggactcgcgtgcgtattgtcgaagagctgttgcgcggc
gaaatgagccagcgtgagttaaaaaatgaactcggcgcaggcatcgcgacgattacgcgtggat
ctaacagcctgaaagccgcgcccgtcgagctgcgccagtggctggaagaggtgttgctgaaaa[
cgattgattttgtaggcctgataagacgtggcgcatcaggcatcgtgcaccgaatgccggatgc
ggcgtga]

Fig. 4 tgcaatatcgggtgctgaccggatatctttacgccgaagtgcccgttttccgtctttgtgtca
atgattgttgacagaaaccttcctgctatccaaatagtgtcatatcatcatattaattgttctt
ttttcaggtgaaggttcccatgcgtctggaagtcttttgtgaagaccgactcggtctgacccgc
gaattactcgatctactcgtgctaaga[gac]attgattacgcggtattgagattgatcccat
tgggcgaatctacctcaatttgctgaactggagtttgagagtttcagcagtctgatggccgaa
atacgccgtattgcgggtgttaccgatgtgcgtactgtcccgtggatgccttccgaacgtgagc
atctggcgttgagcgcgtta[cta]gaggcgttgcctgaacctgtgctctctgtcgatatgaaa
agcaaagtggatatggcgaaccggcgagctgtcagcttttgggcaaaaattggatcgcctgc
gcaaccataccgccgcacaattgattaacggctttaattttttacgttggctggaaagcgaacc
gcaagattcgcataacgagcatgtcgttattaatgggcagaattcctgatggagattacgcct
gtttatcttcaggatgaaaatgatcaacacgtcctgaccggtgcggtggtgatgttgcgatcaa
cgattcgtatgggccgccagttgcaaaatgtcgccgcccaggacgtcagcgccttcagtcaaat
tgtcgccgtcagcccgaaaatgaagcatgttgtcgaacaggcgcagaaactggcgatgctaagc
gcgccgctgctgattacgggtgacacaggtacaggtaaagatctctttgcctacgcctgccatc
aggcaagccccagagcgggcaaaccttacctggcgctgaactgtgcgtctataccggaagatgc
ggtcgagagtgaactgtttggtcatgctccggaagggaagaaaggattctttgagcaggcgaac
ggtggttcggtgctgttggatgaaataggggaaatgtcaccacggatgcaggcgaaattactgc
gtttccttaatgatggcactttccgtcgggttggcgaagaccatgaggtgcatgtcgatgtgcg
ggtgatttgcgctacgcagaagaatctggtcgaactggtgcaaaaaggcatgttccgtgaagat
ctctattatcgtctgaacgtgttgacgctcaatctgccgccgctacgtgactgtccgcaggaca
tcatgccgttaactgagctgttcgtcgcccgctttgccgacgagcagggcgtgccgcgtccgaa
actggccgctgacctgaatactgtacttacgcgttatgcgtggccgggaaatgtgcggcagtta
aagaacgctatctatcgcgcactgacacaactggacggttatgagctgcgtccacaggatattt
tgttgccggattatgacgccgcaacggtagccgtgggcgaagatgcgatggaaggttcgctgga
cgaaatcaccagccgttttgaacgctcggtattaacccagctttatcgcaattatcccagcacg
cgcaaactggcaaaacgtctcggcgtttcacataccgcgattgccaatagttgcgggaatatgg
tctgagtcagaagaagaacgaagagtaagcgcgaatatgcctgatggtgcaacaccatcaggca
tattaaattatgctttcagtacagccagagctgcttcgtaatccggctcggtggtgatttcatc
caccag

E.COLI MUTANT CONTAINING MUTANT GENES RELATED WITH TRYPTOPHAN BIOSYNTHESIS AND PRODUCTION METHOD OF TRYPTOPHAN BY USING THE SAME

TECHNICAL FIELD

The present invention relates to a Tryptophan-producing *E. coli* mutant strain CJ285 (KCCM-10534) containing single or multi mutant genes related with Tryptophan biosynthesis and production method of Tryptophan using the same. More particularly, N-methyl-N'-nitro-N-nitrosoguanidine (hereinafter it will be referred to as NTG) is processed repeatedly, and base sequences and amino acid sequences of genes originated from the Tryptophan-producing mutant gene CJ285, such as aroF and aroG for encoding isoenzyme of DAHP synthase that is resistant to Tryptophan Hydroxamate (hereinafter it will be referred to as THX), the Tryptophan analog, trpR for regulating trp, aroH, mtr, trpR, and aroL operon related with Tryptophan biosynthesis, and tyrR protein for regulating aroF-tyrA, aroG, and aroP operon are known. A mutant strain containing the above gene(s) is then fermented in a medium containing glucose in order to produce L-tryptophan.

BACKGROUND ART

Tryptophan is one of essential amino acids, and has been broadly used in diverse fields including feed additives, medical substances such as sleeping draught or tranquilizer or Ringer's solution, and health food substances. Typical production methods of Tryptophan are chemical synthesis, enzyme reaction, and fermentation using microorganisms. In case of the chemical synthesis, the production takes place in a high temperature and high pressure space, and because D-tryptophan and L-tryptophan are produced together an additional refining process is required to obtain desired tryptophan. In case of the enzyme reaction such as the Japanese patent to Matsui Doatsui (Korean Patent Publication No. 90-005773), indole and serine used as substrates for the reaction are very expensive and the enzyme itself is not safe.

On the other hand, the fermentation using microorganisms involve auxotrophic strains and regulatory mutant strains of diverse microorganisms such as *E. coli* and *Corynebacterium*. Rapid technical advances in gene recombination in 1980's have provided much information on metabolism and control mechanism thereof. Many researchers had remarkable successes to develop superior recombinant strains through gene manipulation, and to improve productivity (Matsui et al, 1988). Also, in Korea, a number of Tryptophan production techniques related with the direct fermentation were disclosed either by using Tryptophan-resistant or auxotrophic mutant strains (Korean Patent Publication Nos. 87-1813, 90-8251, and 92-7405) or recombined strains (Korean Patent Publication Nos. 90-5772 and 91-5627). Mainly these Tryptophan analog resistant strains were to overcome feedback inhibition of enzymes during the Tryptophan biosynthesis, and the recombinant strains were also used for cloning enzymes during the Tryptophan biosynthesis. In fact, the studies have made a remarkable success. For instance, the biggest merit of the traditional L-tryptophan production using an artificial mutant of *E. coli* was that inexpensive cultivation substrates were used to product the L-tryptophan. However, the productivity or the Tryptophan yield was extremely low. Therefore, to maximize the Tryptophan yield through the gene recombination, there exists a need to secure an artificial mutant which is excellent as a parent strain and obtain genes whose regulations are released.

Therefore, the present invention has been made in view of the above problems, and it is an object of the present invention to identify base sequences and amino acid sequences of a mutant gene for encoding aroF and aroG, which are enzymes for use in the synthesis of 3-deoxyarabionohep-tulosonate 7-phosphate (hereinafter it will be referred to as DAHP), the first precursor of aromatic amino acids during the biosynthesis of Tryptophan originated from an *E. coli* mutant strain CJ285, out of phosphoenolpyruvate and Erythorse 4-phosphate, and trpR and tyrR for regulation transcription of genes related with the Tryptophan synthesis.

It is another object of the present invention to provide an L-tryptophan producing *E. coli* mutant strain that contains single or multi mutant genes described above.

It is still another object of the present invention to provide a production method of L-tryptophan with high concentration and high yield by cultivating the mutant directly in a fermentation medium containing glucose.

DESCRIPTION OF THE DRAWINGS

FIG. 1 illustrates a mutant gene (SEQ ID NO: 1), wherein CCT among the internal sequence of aroF gene is mutated to [TCT] and as a result thereof, the $280^{th}$ amino acid Proline is changed to Serine;

FIG. 2 illustrates a mutant gene (SEQ ID NO: 2), wherein T base in the promoter region of aroG gene is mutated to [C] base, GTG in the internal sequence of the gene to [GCG], and TGC to [CGC] and as a result thereof, the $57^{th}$ amino acid Valine is changed to Alanine and the $61^{st}$ amino acid Cysteine is changed to Arginine, respectively;

FIG. 3 illustrates a mutant gene (SEQ ID NO: 3), wherein the $704^{th}$ G base in the internal sequence of trpR gene is deleted and as a result thereof, the frame during the protein translation is changed and 23 amino acids with respect to wild-type gene [cgattgattttgtaggcctgataagacgtggcgcatcaggcatcgtgcaccgaatgccggatgcggcgtga] (SEQ ID NO: 5) are added; and FIG. 4 illustrates a mutant gene (SEQ ID NO: 4), wherein GGC in the internal sequence of tyrR gene is mutated to [GAC] and CTG to [CTA] and as a result thereof, the $25^{th}$ amino acid Glycine is changed to Aspartate and the $86^{th}$ amino acid Leucine is changed to a nonsense mutation.

DISCLOSURE

Technical Problem

In accordance with an aspect of the present invention, the above and other objects can be accomplished by the provision of an *E. coli* mutant strain containing mutant genes related with Tryptophan biosynthesis, in which NTG is processed repeatedly in *E. coli* CJ181 (KFCC 10902), the tryptophan-producing parent strain, to cause mutation therein and the mutant (CJ285) is made resistant to THX, the Tryptophan analog, whereby Tryptophan production of the mutant strain can be improved markedly compared to the parent strain. Also, to analyze DNA base sequence and amino acid sequence, genes for encoding aroF and aroG, the enzymes for synthesizing the first precursor DAHP of the aromatic amino acid during the Tryptophan biosynthesis, trpR protein for regulating trp, aroH, mtr, trpR, and aroL operon related with the Tryptophan biosynthesis, and tyrR protein for regulating aroF-tyrA, aroG, aroP operon are cloned, and the DNA base sequences is compared with the base sequences of wild-type genes. In this manner, it becomes possible to locate gene mutation. Later, CJ285 strain containing at least one of aroF, aroG, trpR and tyrR is cultivated directly in the fermentation medium containing glucose. Compared to the parent strain, the CJ285 produced much more Tryptophan.

That is to say, the *E. coli* CJ285 strain serves to maximize Trypotophan yield through the gene recombination technique and is a novel strain that has never been disclosed. *E. coli* CJ285 has been deposited according to the Budapest treaty under Accession Number KCCM-10534.

TECHNICAL SOLUTION

The present invention provides a production method of L-tryptophan wherein the method includes the steps of: amplifying primer of genes through the Polymerase Chain Reaction (PCR), the genes encoding enzymes involved in the synthesis of 3-deoxyarabionohep-tulosonate 7-phosphate (DAHP), trpR protein for regulating trp, aroH, mtr, trpR, and aroL operon related with Tryptophan biosynthesis, and tyrR protein for regulating aroF-tyrA, aroG, and aroP operon, cloning the genes by pCR2.1-TOPO vector to search plasmid clones that react with a band of expected size; determining base sequences of aroF, aroG, trpR, and tyrR genes based on the bidirectional base sequence analysis employing the plasmid clone containing the above-described four genes as a template, determining amino acid sequences from the base sequences, and comparing the base sequences of the genes with the base sequences of wild-type genes to locate mutation; and fermenting an *E. coli* mutant strain CJ285 containing one or more of mutant genes aroF, aroG, trpR, and tyrR in a fermentation medium containing glucose and thereby, producing L-tryptophan.

The gene manipulation used in the present invention conforms to the Molecular Cloning Laboratory Manual (T. Maniatis E. F., Flitch, J. Sambrook).

A tryptophan-producing parent strain *E. coli* CJ181 (KFCC 10902) was cultivated at constant temperature for five days in a plate minimal medium containing 0.3 g/l of THX, the Tryptophan analog. To increase growth rate and release the sensitivity of the CJ181 to THX, 500 μg/ml of NTG, the mutation-causing substance, was added into the medium. Any strains grown in the minimal medium containing 0.3 g/l of THX were selected first, and these selected strains were cultivated again in a minimal medium containing 0.5 g/l of THX. Finally, a highly THX-resistant strain was selected and named CJ285. The ingredients of the minimal medium are shown in Table 1 below, and 100 mg/l of auxotrophic amino acid was added to the medium, respectively.

TABLE 1

Composition of *E. coli* minimal medium (M9 medium)
Glucose minimal medium (M9 medium)

| Ingredient | Content (g/l) |
|---|---|
| Glucose | 2 |
| NaHPO$_4$ | 6 |
| KH$_2$PO$_4$ | 3 |
| NaCl | 0.5 |
| NH$_4$Cl | 1 |
| MgSO$_4$ | 0.5 |
| CaCl$_2$ | 0.01 |
| Tyrosine | 0.1 |
| pH 7.0 | |

The mutant strain CJ285 of the present invention went through 12-hour shaking culture in LB medium at 37° C. The LB medium (pH=7.4) contained 1% of Bacto-Trypton, 0.5% of Bacto-yeast extract, and 1% of NaCl. Out of the medium was collected a mycobiont and a chromosome DNA was obtained by means of the Quiagen chromosomal DNA isolation kit. Thusly obtained chromosome DNA was immersed in ethanol and dried to be purified. This purified chromosome DNA, being as a template, went through the PCR. Approximately 1.3 kb, 2 kb, 530 bp, and 1.9 kb of aroF, aroG, trpR, and tyrR mutant genes were separated, respectively, from 1% of agarose gel by means of the Quiagen gel extraction kit, and the gene fragments were purified to use as genetic resources for cloning. These mutant gene fragments originated from the CJ285 strain were cloned to pCR2.1-TOTO vector by means of the TOPO cloning kit (manufactured by Invitrogen Company) and as a result thereof, a clone containing the gene was identified.

To determined the base sequence and the amino acid sequence of the gene for encoding aroF, aroG, trpR, and tyrR proteins, the plasmid containing mutant gene(s) was isolated and purified, and the entire gene sequence including the sequence after the promoter, genetic code region, protein synthesis termination codon was determined. In order to determine the DNA base sequence of the genes of the present invention, the previously isolated, purified plasmid DNA was mixed with a sequencing primer and a polymerase, and amplified through the PCR. Thusly amplified plasmid DNA was immersed in ethanol to be purified and mixed with Hi-Di solution. As a result, the plasmid DNA was transformed to a dsDNA containing single strand, and DNA base sequence analysis was proceeded by means of the base sequence analyzer ABI 3100 (manufactured by Applied Biosystem). The DNA base sequence analysis was performed on the basis of the BLAST (http://www.ncbi.nlm.nih.gov/BLAST/) search program in the U.S. NCBI (National Center for Biotechnology Information) website and the Tools PROGRAM (http://us.expasy.org/tools/dna.html) in the ExPasy website. Thusly determined gene base sequence was then compared with the base sequence of a wild-type gene to find out if any mutation occurred, and the mutant amino acid was identified through the translation.

The CJ285 mutant strain containing at least one of the mutant genes aroF, aroG, trpR, and tyrR was fermented directly in the fermentation medium containing glucose to produce L-tryptophan. More specifically, the mutant strain was cultivated under aerobic condition (flask shaking at 200-300 rpm or fermenter at 400-1000 rpm, and the amount of air current=0.5-1.5 vvm), fermentation temperature=30° C. and pH=6.0~8.0, and the resulting L-tryptophan was accumulated into the culture medium. In case of using the flask, the mutant strain was cultivated at 30° C. and 220 rpm for 48-60 hours, and the resulting L-tryptophan was accumulated in the culture medium. In case of using the fermenter, fed batch cultivation is used. Thus, glucose was additionally supplied several times to produce L-tryptophan. The ingredients of the fermentation medium are listed in Table 2 below.

TABLE 2

Composition of fermentation medium

| Fermentation medium in Erlenmeyer flask | | Fermentation medium in 5 L fermenter | |
|---|---|---|---|
| Ingredient | Content (g/l) | Ingredient | Content (g/l) |
| Glucose | 60 | Glucose | 63.16 |
| Yeast extract | 2.5 | Yeast extract | 4 |

TABLE 2-continued

Composition of fermentation medium

| Fermentation medium in Erlenmeyer flask | | Fermentation medium in 5 L fermenter | |
|---|---|---|---|
| Ingredient | Content (g/l) | Ingredient | Content (g/l) |
| $KH_2PO_4$ | 2 | $KH_2PO_4$ | 1.5 |
| $MgSO_4 \cdot 7H_2O$ | 1 | Citric acid | 1.4 |
| $(NH_4)_2SO_4$ | 20 | $MgSO_4 \cdot 7H_2O$ | 2 |
| Sodium citrate | 5 | $(NH_4)_2SO_4$ | 7 |
| NaCl | 1 | Tyrosine | 0.8 |
| Tyrosine | 0.1 | Fumaric acid | 1 |
| $CaCO_3$ | 40 | $CaCl_2$ | 0.5 |

To find out growth rate of the mycobiont of the culture medium, absorbance was measured at 600 nm. Also, the sugar analysis was made based on Bertrand method. Meanwhile, the quantity of L-tryptophan was analyzed by means of HPLC (High Performance Liquid Chromatography).

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

ADVANTAGEOUS EFFECTS

According to the present invention, the novel E. coli mutant strain CJ285 (KCCM-10534) is developed by processing NTG repeatedly in E. coli CJ181, and resistant to Tryptophan Hydroxamate, the Tryptophan analog. By analyzing DNA base sequence and amino acid of mutant genes aroF, aroG, trpR, and tyrR related with Tryptophan biosynthesis, a significant mutation can be identified and a proper mutant gene for use in the recombined strain development can be obtained. In addition, compared to the parent strain CJ181, its mutant strain CJ285 containing at least one of the mutant genes is capable of producing more Tryptophan (about 10% more). Therefore, CJ285 of the present invention can be very advantageously used as a proper mother strain for the recombined strain development and for the amino acid fermentation industry and pharmaceutical manufacture.

MODE FOR CARRYING OUT THE INVENTION

Example 1

Selection of THX-Resistant Mutant Strain CJ285

Tryptophan-producing parent strain E. coli CJ181 (KFCC 10902) went through 12-hour shaking culture in LB medium at 37° C., and was rinsed twice in sterilized saline solution. Here, the LB medium (pH=7.4) contained 1% of Bacto-Trypton, 0.5% of Bacto-yeast extract, and 1% of NaCl. The CJ181 was diluted in 0.1M sodium citrate buffer solution (pH=5.5) until the final OD=1.0. The CJ181 was cultivated in the minimal medium containing 0.3 g/l of THX (please refer to Table 1) for five days. In order to increase growth rate and make the THX-resistant CJ181, 500 µg/ml of NTG, the mutation-causing substance, was added into the medium. The solution was placed in a 37° C. thermostatic bath for the reaction for 30 minutes, and was rinsed in 0.1M phosphate buffer solution (pH=7.0) three times. Then the CJ181 was cultivated in a minimal medium containing 0.5 g/l of THX (please refer to Table 1) for five days and as a result thereof, approximately 100 colonies were obtained. Thusly obtained mutant strains and the original parent strain were subject to Tryptophan fermentation test in a flask. In result, E. coli CJ285 featuring superior tryptophan production capacity to the original E. coli parent strain CJ181 could be selected. The best strain for producing L-tryptophan was isolated from the strains, and placed in an Erlenmeyer flask. After conducting the tryptophan production test on the strain in the flask, and the fermentation experiment in the 5 L fermenter was performed as described in Example 6 below.

TABLE 3

| Experiment result of newly developed artificial mutant strains in flask | | |
|---|---|---|
| E. coli | Mycobiant ($OD_{600}$) | L-tryptophan (g/l) |
| CJ181 | 30 | 7.1 |
| CJ285 | 28 | 7.9 |

As seen in Table 3, the concentration of L-tryptophan produced from the E. coli mutant strain CJ285 was higher than that of the original parent strain E. coli KFCC 10902. The CJ285 was deposited with the KCCM (Korean Culture Center of Microorganisms) on Nov. 28, 2003, and given the number KCCM-10534.

Example 2 aroF Gene Cloning of Mutant Strain CJ285 And Sequence Analysis

To amplify aroF gene through the PCR using a chromosome DNA isolated from the CJ285 as a template, the following primers (21-mers) were used. 5'-GTATTTACCCCGT-TATTGTC-3' (SEQ ID NO: 6) was used as a sense primer, and 5'-CACTTCAGCAACCAGTTCCAG-3' (SEQ ID NO: 7) was used as an anti-sense primer. For the PCR about 30 ng of genomic DNA of the CJ285 and 25 pmol of each primer were added to Accupower PCR HL-Premix containing DNA polymerase, dNTPs and reaction buffer until the final concentration becomes 20 µl. The PCR program was executed 25 times. It started at 94° C. for five minutes and then 35 seconds, at 55° C. for 40 seconds, and at 72° C. for 90 seconds. Lastly, the last extension was performed for seven minutes at 72° C. Its result was then checked through 1% agarose gel electrophoresis.

To clone the gene fragment to pCR2.1-TOPO vector, about 1.3 kb (which corresponds to the size of aroF mutant gene) gene fragments were isolated from the 1% agarose gel by means of the Quiagen gel extraction kit. Thusly obtained gene fragments were then purified and used as genetic resources for cloning. By using the TOPO cloning kit (manufactured by Invitrogen Company) the mutant gene fragments obtained form the CJ285 strain were mixed with pCR2.1-TOPO vector solution at the ratio of 1:4. Later, 1 µl of saline solution was added to the mixture and the reaction was continued at room temperature for 20 minutes. The reaction solution was mixed with 40 µl of TOP10 competent cell included in the kit and sit in the ice for 20 minutes. Afterwards, thermal shock was applied for 30 seconds at 42° C. and the solution was placed back to the ice immediately for 2 minutes. 250 µl of SOC medium was added thereto, and the mutant genes were cultivated at 37° C. for 1 hour. 100 µl of culture medium was smeared over LB agar medium containing 50 µg/ml of Ampicillin, and the mutant genes were cultivated therein for about 12 hours at 37° C. Only white colonies were selected and cultivated again for about 12 hours in the LB liquid medium containing 50 µg/ml of Ampicillin. Plasmid was isolated therefrom and treated with EcoRI restriction enzyme for 2 hours and developed by 1% agarose gel electrophoresis. By using an UV illuminator, a clone containing the mutant gene(s) was identified.

To determine DNA base sequence of the genes, plasmid was isolated from the previously identified clone and purified. Thusly isolated, purified plasmid was mixed with 2 pmol of sequence analysis primer that can be combined with aroF gene through a complementary hydrogen bond, 2 µl of Big dye containing polymerase, and 1 µl of plasmid DNA (about 200 ng). Then, the PCR was executed 25 times, first at 96° C. for 30 seconds, at 50° C. for 15 seconds, and at 60° C. for four minutes. The plasmid DNA was immersed in ethanol to be purified and mixed with 10 µl of Hi-Di solution. As a result, the plasmid DNA was transformed to a dsDNA containing single strand, and DNA base sequence analysis was proceeded by means of the base sequence analyzer ABI 3100 (manufactured by Applied Biosystem). The DNA base sequence analysis was performed on the basis of the BLAST (http://www.ncbi.nlm.nih.gov/BLAST/) search program in the U.S. NCBI (National Center for Biotechnology Information) website and the Tools PROGRAM (http://us.expasy.org/tools/dna.html) in the ExPasy website. Thusly determined gene base sequence was then compared with the base sequence of a wild-type gene to find out if any mutation occurred, and the mutant amino acid was identified through the translation.

Example 3 aroG Gene Cloning of Mutant Strain CJ285 and Sequence Analysis

To amplify aroG gene through the PCR using a chromosome DNA isolated from the CJ285 as a template, the following primers (21-mers) were used. 5'-GTATTTACCCCGT-TATTGTC-3' (SEQ ID NO: 6) was used as a sense primer, and 5'-ACTCCGCCGGAAGTGACTAA-3' (SEQ ID NO: 8) was used as an anti-sense primer. For the PCR about 30 ng of genomic DNA of the CJ285 and 25 pmol of each primer were added to Accupower PCR HL-Premix containing DNA polymerase, dNTPs and reaction buffer until the final concentration becomes 20 µl. The PCR program was executed 25 times. It started at 94° C. for five minutes and then 35 seconds, at 55° C. for 40 seconds, and at 72° C. for two minutes and 20 seconds. Lastly, the last extension was performed for seven minutes at 72° C. Its result was then checked through 1% agarose gel electrophoresis.

Example 4 trpR Gene Cloning of Mutant Strain CJ285 and Sequence Analysis

To amplify trpR gene through the PCR using a chromosome DNA isolated from the CJ285 as a template, the following primers (21-mers) were used. 5'-CGCCACG-GAATGGGGACGTCG-3' (SEQ ID NO: 9) was used as a sense primer, and 5'-CCGCGTCTTATCATGCCTACC-3' (SEQ ID NO: 10) was used as an anti-sense primer. For the PCR about 30 ng of genomic DNA of the CJ285 and 25 pmol of each primer were added to Accupower PCR HL-Premix containing DNA polymerase, dNTPs and reaction buffer until the final concentration becomes 20 µl. The PCR program was executed 25 times. It started at 94° C. for five minutes and then 1 minute, at 60° C. for 30 seconds, and at 72° C. for 1 minute. Lastly, the last extension was performed for seven minutes at 72° C. Its result was then checked through 1% agarose gel electrophoresis.

Example 5 tyrR Gene Cloning of Mutant Strain CJ285 and Sequence Analysis

To amplify tyrR gene through the PCR using a chromosome DNA isolated from the CJ285 as a template, the following primers (21-mers) were used. 5'-GGATTGACGATGA-CAAACCT-3' (SEQ ID NO: 11) was used as a sense primer, and 5'-CTGGTGGATGAAATCACCAC-3' (SEQ ID NO: 12) was used as an anti-sense primer. For the PCR about 30 ng of genomic DNA of the CJ285 and 25 pmol of each primer were added to Accupower PCR HL-Premix containing DNA polymerase, dNTPs and reaction buffer until the final concentration becomes 20 µl. The PCR program was executed 25 times. It started at 94° C. for five minutes and then 1 minute, at 53° C. for 30 seconds, and at 72° C. for two minutes and 20 seconds. Lastly, the last extension was performed for seven minutes at 72° C. Its result was then checked through 1% agarose gel electrophoresis.

To clone the gene fragment to pCR2.1-TOPO vector, about 1.9 kb (which corresponds to the size of tyrR mutant gene) gene fragments were isolated by means of the Quiagen gel extract kit. Thusly obtained gene fragments were then purified and used as genetic resources for cloning. The experiment procedure from this point and the base sequence analysis following the determination of base sequence are identical with those in Example 2.

Example 6

Fermentation of Mutant Strain CJ285 in 5 L Fermenter

*E. coli* CJ285 containing at least one of the mutant genes with the base sequence disclosed in the Examples 2 to 5, and the parent strain CJ181 (KFCC 10902) were fed batch cultivated in a 5 L fermenter (fermentation temperature=30° C., culture pH=6.9-7.1 (pH can be controlled by ammonia water), the amount of air current=0.5-1.0 vvm, and stirring speed=500-700 rpm). It turned out the fermentation concentration of the CJ285 was 28.2 g/l, and that of the parent strain CJ181 was 25.1 g/l. Therefore, the fermentation time of the *E. coli* CJ285 was reduced slightly, resulting in L-tryptophan productivity increase by about 10% per hour.

TABLE 4

Fermentation of CJ285 mutant strain in 5 L fermenter

| Name of strain | Cultivation time (hr) | Total sugar (g/l) | Total amount of accumulated T-tryptophan |
|---|---|---|---|
| CJ181 | 63 | 243.5 | 25.1 |
| CJ285 | 61 | 243.5 | 28.2 |

The invention claimed is:

1. An isolated L-tryptophan producing *E. coli* CJ285 KCCM-10534 containing at least one of mutant genes consisting of aroF, aroG, trpR, and tyrR related with Tryptophan biosynthesis.

2. A production method of L-tryptophan comprising fermenting the *E. coli* mutant strain of claim 1 in a fermentation medium to produce L-tryptophan.

* * * * *

SEQUENCE LISTING

<160> NUMBER OF SEQ ID NOS: 12

<210> SEQ ID NO 1
<211> LENGTH: 1326
<212> TYPE: DNA
<213> ORGANISM: Escherichia coli

<400> SEQUENCE: 1

```
cagaggtaag ggttgaaagc gcgactaaat tgcctgtgta aataaaaatg tacgaaatat      60
ggattgaaaa ctttacttta tggtatcgtt acgtcgtcct cgctgaggat caactatcgc     120
aaacgagcat aaacaggatc gccatcatgc aaaagacgc gctgaataac gtacatatta     180
ccgacgaaca ggttttaatg actccggaac aactgaaggc cgcttttcca ttgagcctgc    240
aacaagaagc ccagattgct gactcgcgta aaagcatttc agatattatc gccgggcgcg    300
atcctcgtct gctggtagta tgtggtcctt gttccattca tgatccggaa actgctctgg    360
aatatgctcg tcgatttaaa gcccttgccg cagaggtcag cgatagcctc tatctggtaa    420
tgcgcgtcta ttttgaaaaa ccccgtacca ctgtcggctg aaagggtta attaacgatc     480
cccatatgga tggctctttt gatgtagaag ccgggctgca gatcgcgcgt aaattgctgc    540
ttgagctggt gaatatggga ctgccactgg cgacggaagc gttagatccg aatagccccgc   600
aatacctggg cgatctgttt agctggtcag caattggtgc tcgtacaacg gaatcgcaaa    660
ctcaccgtga aatggcctcc gggctttcca tgccggttgg ttttaaaaac ggcaccgacg    720
gcagtctggc aacagcaatt aacgctatgc gcgccgccgc ccagccgcac cgttttgttg    780
gcattaacca ggcagggcag gttgcgttgc tacaaactca ggggaatccg gacggccatg    840
tgatcctgcg cggtggtaaa gcgccgaact atagccctgc ggatgttgcg caatgtgaaa    900
aagagatgga acaggcggga ctgcgcccgt ctctgatggt agattgcagc cacgtaatt    960
ccaataaaga ttatcgccgt cagtctgcgg tggcagaatc cgtggttgct caaatcaaag   1020
atggcaatcg ctcaattatt ggtctgatga tcgaaagtaa tatccacgag gcaatcagt   1080
cttccgagca accgcgcagt gaaatgaaat acggtgtatc cgtaaccgat gcctgcatta   1140
gctgggaaat gaccgatgcc ttgctgcgtg aaattcatca ggatctgaac gggcagctga   1200
cggctcgcgt ggcttaagag gtttattatg gttgctgaat tgaccgcatt acgcgatcaa   1260
attgatgaag tcgataaagc gctgctgaat ttattagcga agcgtctgga actggttgct   1320
gaagtg                                                              1326
```

<210> SEQ ID NO 2
<211> LENGTH: 1590
<212> TYPE: DNA
<213> ORGANISM: Escherichia coli

<400> SEQUENCE: 2

```
acagtcagaa ataatgtggc cagttttgtc attttcatag gatgctcctg ttatggtcgt      60
tatgtcggat aacctcttcc aacagtgcat ttgcaggtga atataaggca ttggtttaag    120
atttcagcca ggttatgaaa cgcagcagag aatcttgaaa taattaacaa acaaaggagt    180
tacagttaga aattgtagga gagatctcgt ttttcgcgac aatctggcgt ttttcttgct    240
aattccagga ttaatccgtt catagtgtaa aaccccgttt acacattctg acggaagata    300
tagattggaa gtattgcatt cactaagata agtatggcaa cactggaaca gacatgaatt    360
atcagaacga cgatttacgc atcaaagaaa tcaaagagtt acttcctcct gtcgcattgc    420
```

```
tggaaaaatt ccccgctact gaaaatgccg cgaatacggt tgcccatgcc cgaaaagcga      480
tccataagat cctgaaaggt aatgatgatc gcctgttggt tgcgattggc ccacgctcaa      540
ttcatgatcc tgtcgcggca aaagagtatg ccactcgctt gctggcgctg cgtgaagagc      600
tgaaagatga gctggaaatc gtaatgcgcg tctattttga aaagccgcgt accacggtgg      660
gctggaaagg gctgattaac gatccgcata tggataatag cttccagatc aacgacggtc      720 tgccgtatagc ccgtaaattg ctgcttgata ttaacgacag cggtctgcca gcggcaggtg     780
agtttctcga tatgatcacc ccacaatatc tcgctgacct gatgagctgg ggcgcaattg      840
gcgcacgtac caccgaatcg caggtgcacc gcgaactggc atcagggctt tcttgtccgg      900
tcggcttcaa aaatggcacc gacggtacga ttaaagtggc tatcgatgcc attaatgccg      960
ccggtgcgcc gcactgcttc ctgtccgtaa cgaaatgggg gcattcggcg attgtgaata     1020
ccagcggtaa cggcgattgc catatcattc tgcgcggcgg taaagagcct aactacagcg     1080
cgaagcacgt tgctgaagtg aaagaagggc tgaacaaagc aggcctgcca gcacaggtga     1140
tgatcgattt cagccatgct aactcgtcca acaattcaa aaagcagatg gatgtttgtg      1200
ctgacgtttg ccagcagatt gccggtggcg aaaaggccat tattggcgtg atggtggaaa     1260
gccatctggt ggaaggcaat cagagcctcg agagcgggga gccgctggcc tacggtaaga     1320
gcatcaccga tgcctgcatc ggctgggaag ataccgatgc tctgttacgt caactggcga     1380
atgcagtaaa agcgcgtcgc gggtaaggtt taattgtcgg atgcgccgtc agagtggcgt     1440
atccgatgaa tcaccacagg cctgataagt cgcgcagcgc cgcatcaggc aatgtgctcc     1500
attgttagca acaaaaaagc cgactcactt gcagtcggct ttctcatttt aacgaatgac     1560
gtttacttcg ctttaccctg gtttgcaacc                                      1590

<210> SEQ ID NO 3
<211> LENGTH: 390
<212> TYPE: DNA
<213> ORGANISM: Escherichia coli

<400> SEQUENCE: 3
atggcccaac aatcacccta ttcagcagcg atggcagaac agcgtcacca ggagtggtta      60
cgttttgtcg acctgcttaa gaatgcctac caaaacgatc tccatttacc gttgttaaac     120
ctgatgctga cgccagatga gcgcgaagcg ttggggactc gcgtgcgtat tgtcgaagag     180
ctgttgcgcg gcgaaatgag ccagcgtgag ttaaaaaatg aactcggcgc aggcatcgcg     240
acgattacgc gtggatctaa cagcctgaaa gccgcgcccg tcgagctgcg ccagtggctg     300
gaagaggtgt tgctgaaaac gattgatttt gtaggcctga taagacgtgg cgcatcaggc     360
atcgtgcacc gaatgccgga tgcggcgtga                                      390

<210> SEQ ID NO 4
<211> LENGTH: 1794
<212> TYPE: DNA
<213> ORGANISM: Escherichia coli

<400> SEQUENCE: 4
tgcaatatcg ggtgctgacc ggatatcttt acgccgaagt gcccgttttt ccgtctttgt      60
gtcaatgatt gttgacagaa accttcctgc tatccaaata gtgtcatatc atcatattaa     120
ttgttctttt ttcaggtgaa ggttcccatg cgtctggaag tcttttgtga agaccgactc     180
ggtctgaccc gcgaattact cgatctactc gtgctaagag acattgattt acgcggtatt     240
```

```
gagattgatc ccattgggcg aatctacctc aattttgctg aactggagtt tgagagtttc    300
agcagtctga tggccgaaat acgccgtatt gcgggtgtta ccgatgtgcg tactgtcccg    360
tggatgcctt ccgaacgtga gcatctggcg ttgagcgcgt tactagaggc gttgcctgaa    420
cctgtgctct ctgtcgatat gaaaagcaaa gtggatatgg cgaacccggc gagctgtcag    480
cttttttggc aaaaattgga tcgcctgcgc aaccataccg ccgcacaatt gattaacggc    540
tttaattttt tacgttggct ggaaagcgaa ccgcaagatt cgcataacga gcatgtcgtt    600
attaatgggc agaatttcct gatggagatt acgcctgttt atcttcagga tgaaaatgat    660
caacacgtcc tgaccggtgc ggtggtgatg ttgcgatcaa cgattcgtat gggccgccag    720
ttgcaaaatg tcgccgccca ggacgtcagc gccttcagtc aaattgtcgc cgtcagcccg    780
aaaatgaagc atgttgtcga acaggcgcag aaactggcga tgctaagcgc gccgctgctg    840
attacgggtg acacaggtac aggtaaagat ctctttgcct acgcctgcca tcaggcaagc    900
cccagagcgg gcaaacctta cctggcgctg aactgtgcgt ctataccgga agatgcggtc    960
gagagtgaac tgtttggtca tgctccggaa gggaagaaag gattctttga gcaggcgaac   1020
ggtggttcgg tgctgttgga tgaaataggg gaaatgtcac cacggatgca ggcgaaatta   1080
ctgcgtttcc ttaatgatgg cactttccgt cgggttggcg aagaccatga ggtgcatgtc   1140
gatgtgcggg tgatttgcgc tacgcagaag aatctggtcg aactggtgca aaaaggcatg   1200
ttccgtgaag atctctatta tcgtctgaac gtgttgacgc tcaatctgcc gccgctacgt   1260
gactgtccgc aggacatcat gccgttaact gagctgttcg tcgcccgctt tgccgacgag   1320
cagggcgtgc cgcgtccgaa actggccgct gacctgaata ctgtacttac gcgttatgcg   1380
tggccgggaa atgtgcggca gttaaagaac gctatctatc gcgcactgac acaactggac   1440
ggttatgagc tgcgtccaca ggatattttg ttgccggatt atgacgccgc aacggtagcc   1500
gtgggcgaag atgcgatgga aggttcgctg gacgaaatca ccagccgttt tgaacgctcg   1560
gtattaaccc agctttatcg caattatccc agcacgcgca aactggcaaa acgtctcggc   1620
gtttcacata ccgcgattgc caatagttgc gggaatatgg tctgagtcag aagaagaacg   1680
aagagtaagc gcgaatatgc ctgatggtgc aacaccatca ggcatattaa attatgcttt   1740
cagtacagcc agagctgctt cgtaatccgg ctcggtggtg atttcatcca ccag          1794
```

<210> SEQ ID NO 5
<211> LENGTH: 71
<212> TYPE: DNA
<213> ORGANISM: Escherichia coli

<400> SEQUENCE: 5

```
cgattgattt tgtaggcctg ataagacgtg gcgcatcagg catcgtgcac cgaatgccgg    60
atgcggcgtg a                                                        71
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
gtatttaccc cgttattgtc                                                20
```

<210> SEQ ID NO 7

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cacttcagca accagttcca g                                              21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
actccgccgg aagtgactaa                                                20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgccacggaa tggggacgtc g                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccgcgtctta tcatgcctac c                                              21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggattgacga tgacaaacct                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctggtggatg aaatcaccac                                                20
```